US011877717B2

United States Patent
Ruccio

(10) Patent No.: US 11,877,717 B2
(45) Date of Patent: *Jan. 23, 2024

(54) METHOD AND APPARATUS FOR DETECTING SCOLIOSIS

(71) Applicant: Emma Ruccio, Southington, CT (US)

(72) Inventor: Emma Ruccio, Southington, CT (US)

( * ) Notice: Subject to any disclaimer, the term of this patent is extended or adjusted under 35 U.S.C. 154(b) by 49 days.

This patent is subject to a terminal disclaimer.

(21) Appl. No.: 17/877,548

(22) Filed: Jul. 29, 2022

(65) Prior Publication Data

US 2022/0378365 A1 Dec. 1, 2022

Related U.S. Application Data

(63) Continuation-in-part of application No. 17/124,397, filed on Dec. 16, 2020, now Pat. No. 11,423,574.

(Continued)

(51) Int. Cl.
*A61B 5/00* (2006.01)
*G06T 7/00* (2017.01)
(Continued)

(52) U.S. Cl.
CPC .......... *A61B 5/4561* (2013.01); *A61B 5/0077* (2013.01); *A61B 5/015* (2013.01);
(Continued)

(58) Field of Classification Search
CPC . G06T 2207/10016; G06T 2207/10048; G06T 2207/20081; G06T 2207/30012; G06T 7/0016; G06T 7/80
See application file for complete search history.

(56) References Cited

U.S. PATENT DOCUMENTS 11,423,574 B2 8/2022 Ruccio
2014/0030352 A1 10/2014 Akimoto et al.
(Continued)

FOREIGN PATENT DOCUMENTS

CN 107481228 12/2017
CN 110415291 A * 11/2019
(Continued)

OTHER PUBLICATIONS

Publisher: LADYBUG04, Got Your Back: 2.0—NICEE 2018 in Dearborn, MI, posted on May 12, 2018, (https://www.youtube.com/watch?v=xIKKtl0GQek&feature=youtu.be); 1 pp.
(Continued)

*Primary Examiner* — Dakshesh D Parikh
(74) *Attorney, Agent, or Firm* — UConn IP Law Clinic; Nolyn Allen; Adam Burns

(57) ABSTRACT

A computer-implemented method of detecting and quantifying a spinal curve is disclosed herein. The method comprises obtaining an infrared radiometer camera, positioning the infrared radiometer camera for receiving thermal data for a spine of a subject, the camera being horizontally spaced about ½ meters to about 3 meters from the spine, scanning at least a portion of the spine with the infrared radiometer camera to obtain the thermal data, analyzing the thermal data using machine learning software which uses a classification algorithm to determine the presence of the spinal curve, and calculating a first Cobb angle for the curve of the subject's spine. Corresponding systems and additional methods also are disclosed.

13 Claims, 6 Drawing Sheets

Related U.S. Application Data

(60) Provisional application No. 62/949,066, filed on Dec. 17, 2019.

(51) Int. Cl.
  *A61B 5/01* (2006.01)
  *A61B 5/107* (2006.01)
  *H04M 1/724* (2021.01)

(52) U.S. Cl.
  CPC .......... *A61B 5/1079* (2013.01); *A61B 5/7267* (2013.01); *A61B 5/7282* (2013.01); *G06T 7/0016* (2013.01); *G06T 2207/10048* (2013.01); *G06T 2207/20081* (2013.01); *G06T 2207/20084* (2013.01); *G06T 2207/30012* (2013.01); *H04M 1/724* (2021.01)

(56) References Cited

U.S. PATENT DOCUMENTS

| | | | | |
|---|---|---|---|---|
| 2015/0071513 | A1* | 3/2015 | Arnon | G06V 10/25 382/128 |
| 2018/0053352 | A1 | 2/2018 | Finding et al. | |

FOREIGN PATENT DOCUMENTS

| | | | | |
|---|---|---|---|---|
| JP | 2010259452 | A | * 11/2010 | ............ A61B 6/563 |
| KR | 2013102784 | A | * 9/2013 | |
| WO | WO2009/001357 | | 12/2008 | |
| WO | WO2013/081030 | | 6/2013 | |
| WO | WO2014/043661 | | 3/2014 | |
| WO | WO2014079812 | A1 | 5/2014 | |

OTHER PUBLICATIONS

Wallingford and Southington students win awards (https://www.myrecordjournal.com/News/Front-Porch/FPN-NICEE-RJ-072218.html), published on Jun. 16, 2018; 14 pp.

An Academy That Teaches Science by Focusing on Social Impact (https://cptv.org/atwonders-peak/), published on Oct. 16, 2018; 6 pp.

Papapouliou et al., Thermographic Image Analysis in Scoliosis, Abstracts / Physica Medica 32 (2016) 284-339 (http://dx.doi.org/10.1016/j.ejmp.2016.07.216), Sep. 1, 2016; 3 pp.

Kwok et al., Postural Screening for Adolescent Idiopathic Scoliosis with Infrared Thermography, Scientific Reports, 7: 14431, DOI:10.1038/s41598-017-14556-w (Oct. 31, 2017) (https://www.researchgate.net/publication/320736954_Postural_Screening_for_Adolescent_Idiopathic_Scoliosis_with_Infrared_Thermography); 7 pp.

Fane De Salis et al., Medical & Biological Engineering & Computing, (https://doi.org/10.1007/s11517-018-1806-3), published online Feb. 26, 2018; 36 pp., Evaluation of high resolution thermal imaging to determine the effect of vertebral fractures on associated skin surface temperature in children with osteogenesis imperfect.

Hildebrandt et al., An Overview of Recent Application of Medical Infrared Thermography in Sports Medicine in Austria, Sensors (2010), 10, 4700-4715; doi:10.3390/s100504700 (https://www.researchgate.net/publication/223134122_An_Overview_of_Recent_Application_of_Medical_Infrared_Thermography_in_Sports_Medicine_in_Austria); 10 pp.

Top 300 Masters 2018; Broadcom Masters; https://sspcdn.blob.core.windows.net/files/Documents/SEP/BCM/2018/Program-Books/Top-300-MASTERS.pdf; 3 pp.

2018 CIC Finals Recognized Inventors; https://www.ctinventionconvention.org/images/Documents/2018Docs/2018-Recognized-Inventors.pdf; 6 pp.

Facebook Post by Talcott Mountain Science Center & Academy; Jun. 5, 2018; 1 pp https://www.facebook.com/talcottscience/photos/congratulations-to-talcott-mountain-academy-8th-graders-emma-ruccio-and-julian-k/1567200543402732/.

Connecticut Student Writers; University of Connecticut; 2017; https://cwp.uconn.edu/wp-content/uploads/sites/191/2017/05/CSWMagazineFinal2017.3.pdf; 3 pp.

2018 Top 300 Masters by Fair ID; Society for Science; https://www.societyforscience.org/broadcom-masters/2018-top-300-masters-by-fair-id/; 3 pp.

Congratulations to the Top 300 Masters !; Society for Science; https://www.societyforscience.org/broadcom-masters/2018-top-300-masters/; 5 pp.

Congratulations Broadcom Masters!; Science News; https://www.sciencenewsdigital.org/sciencenews/september15_2018?pg=27#pg27; 1 pp.

Facebook post by Arrow Electronics; Jul. 20, 2018; 1 pp https://www.facebook.com/arrowfiveyearsout/posts/video-watch-emma-ruccio-winner-of-the-arrow-electronics-innovation-in-electronic/1772318066177215/.

National Invention Convention & Entrepreneurship Expo (NICEE) 2018 Award Winners; https://www.ctinventionconvention.org/images/Documents/2018Docs/2018NICEEWinners.pdf Jun. 1, 2018; 2 pp.

Arrow Electronics on Twitter: Video: Watch Emma Ruccio, winner of the Arrow Electronics Innovation in Electronics Award, talk about how her #scoliosis diagnostics tool "Got Your Back 2.0" reduces harmful radiation exposure and costly office visits. https—Arrow Electronics; Jul. 20, 2018; 1 pp; https://www.companyowl.com/i/t/arrow-electronics-twitter-video-watch-emma-ruccio-winner-arrow-electronics-innovation-electronics-award-talk-scoliosis-diagnostics-tool-got-20-reduces-harmful-radiation-exposure-costly-office-visits-https/6607931.

Talcott Mountain Science Center; Talcott Mountain Academy Students Selected as Two of the Top 300 Young Scientists in the US; https://www.tmsc.org/news-media/press; Oct. 10, 2018; 3 pp.

Dan Amarante; Talcott Mountain Academy Shout Out Invention Winners; https://www.youtube.com/watch?app=desktop&v=BK_AmJhOTfo&ab_channel=DanAmarante; Jun. 5, 2018; 2 pp.

Dan Amarante; Talcott Mountain Academy Invention Convention; https://www.youtube.com/watch?app=desktop&v=jWPUzYhMMDo&ab_channel=DanAmarante; Jun. 7, 2018; 2 pp.

Arrow Electronics Launches 2018 Innovation in Technology Awards; Arrow Electronics; Jul. 10, 2018; 3 pp; https://www.3blmedia.com/News/Arrow-Electronics-Launches-2018-Innovation-Technology-Awards#:~:text=Arrow%20Electronics%20presented%20eighth%20grader,compete%.

Magazine Article by Arrow Electronics: A Next-Generation Edison; https://www.arrow.com/en/research-and-events/articles/a-next-generation-edison; Apr. 9, 2019; 13 pp.

Facebook; Arrow Electronics; Jul. 13, 2018; 1 pp https://www.facebook.com/arrowfiveyearsout/photos/we-were-proud-to-present-emma-ruccio-an-eighth-grader-from-connecticut-with-our-/1762076140534741/.

Twitter post by Arrow Electronics; https://twitter.com/arrowglobal/status/1020328985459331072; Jul. 20, 2018; 1 pp.

Talcott Mtn Academy Students Win at National Invention Convention; Christine Buhler; Jun. 8, 2018; 4 pp https://patch.com/connecticut/avon/talcott-mtn-academy-students-win-national-invention-convention.

Four of our 8th Grade Inventors at NICEE; Jonathan Craig; https://www.linkedin.com/pulse/four-our-8th-grade-inventors-nicee-jonathan-craig/; Jun. 5, 2018; 3 pp.

Jeong et al., Study on the Diagnostic System of Scoliosis by using Infrared Camera, Bio-Medical Materials and Engineering 26 (2015) S1193- S1199 DOI 10.3233/BME-151416 (https://www.ncbi.nlm.nih.gov/pubmed/26405878); 1 pp.

Dyszkiewicz et al., Simplified Analysis of Spine Thermovision Picture in Diagnostics of Scoliosis, Acta of Bioengineering and Biomechanics, vol. 3, No. 1, 2001 (http://yadda.icm.edu.pl/yadda/element/bwmeta1.element.baztech-article-BPB1-0013-0029); 1 pp.

Major et al., Depth Sensors in Screening of Scoliosis, Biomechanica Hungarica VI. évfolyam, 1. Szám, 2003 (https://www.researchgate.net/publication/276904191_Depth_sensors_in_screening_of_scoliosis); 4 pp.

(56) References Cited

OTHER PUBLICATIONS

Ibarra-Castanedo et al., Infrared Image Processing and Data Analysis, Infrared Physics & Technology 46 (2004) 75-83 (https://www.researchgate.net/publication/223050515_Infrared_image_processing_and_data_analysis); 14 pp.

Jocic et al., Linear Fuzzy Space Based Scoliosis Screening, ICIST 2014—vol. 1 Regular papers (https://www.researchgate.net/publication/268151080_Linear_Fuzzy_Space_Based_Scoliosis_Screening); 6 pp.

422. Talcott Mountain Science Center & Academy; https://www.ctmq.org/422-talcott-mountain-science-center/; May 24, 2019; 34 pp.

CT Science Fair; Project List 2018 Connecticut Science & Engineering Fair Broadcom Winners; CT Science Fair; http://ctsciencefair.org/media/2018Broadcom.pdf; 2 pp.

Testimony of Danny Briere, Chief Entrepreneurship Officer of the Henry Ford and Global Director of Invention Convention Worldwide on the Success Act of 2018 USPTO Detroit Office; https://www.uspto.gov/sites/default/files/documents/SUCCESSAct-The-Henry-Ford.pdf; Jun. 18, 2019; 7 pp.

55 Connecticut Students to Compete in National Invention Convention; Kaitlyn McGrath; May 13, 2016; 3 pp https://www.nbcconnecticut.com/news/local/55-connecticut-students-to-compete-in-national-invention-convention/56905/.

Arrow Electronics Launches 2018 Innovation in Technology Awards; Justmeans; http://www.justmeans.com/blog/arrow-electronics-launches-2018-innovation-in-technology-awards Jul. 10, 2018; 2 pp.

Wallingford, Southington, Cheshire students compete in national invention convention; Bailey Wright; Jun. 16, 2018; 5 pp from prior box https://www.myrecordjournal.com/News/State/Local-students-take-home-awards-at-national-invention-convention.html https://www.3blmedia.com/News/VIDEO-Arrow-Electronics-2018-Innovation-Electronics-Award-Winner.

CSEF "Spirit of Innovation Awards" at 2017 CT Invention Convention; CT Science Fair; May 9, 2017; 3 pp http://ctsciencefair.org/2017/csef-spirit-of-innovation-awards-at-2017-ct-invention-convention.

2018 Broadcom Masters Semifinalists Announced; CT Science Fair; http://ctsciencefair.org/2018/2018-broadcom-masters-semifinalists-announced; Oct. 7, 2018; 6 pp.

Talcott Mountain Academy Students Receive Awards at Connecticut Invention Convention; Move on to National Competition; Talcott Mountain Science Center; May 2, 2018; 4 pp https://www.tmsc.org/content/talcott-mountain-academy-students-receive-awards-connecticut-invention-convention-move.

Public Hearing on the "Success Act"; USPTO; https://www.uspto.gov/sites/default/files/documents/SUCCESS-Act-transcript-Detroit-MI-061819.pdf ; Jun. 18, 2019; 6 pp.

Looking for a sensor to daisy chain for angles; jspita; https://forums.adafruit.com/viewtopic.php?f=25&t=107622; Jan. 24, 2015; 17 pp.

Connecticut Science & Engineering Fair; DOCBOX; https://educationdocbox.com/75628559-English_as_a_2nd_Language/Connecticut-science-engineering-fair.html; 3 pp.

Area students present at National Invention Convention; Bailey Wright; https://issuu.com/southingtoncitizen/docs/southingtoncitizen20180622; Jun. 22, 2018; 1 pp.

Video | Arrow Electronics 2018 Innovation in Electronics Award Winner; Arrow Electronics; Jul. 16, 2018; 2 pp.

* cited by examiner

METHOD AND APPARATUS FOR DETECTING SCOLIOSIS

RELATED APPLICATIONS

This is a continuation-in-part of U.S. application Ser. No. 17/124,397 filed Dec. 16, 2020, which in turn claims the benefit of U.S. Provisional Application No. 62/949,066 filed Dec. 17, 2019.

BACKGROUND

1. Field of the Invention

This invention is in the field of apparatus for diagnosing medical conditions and pertains more particularly to a method to detect and quantify scoliosis.

2. Description of Related Art

Scoliosis is a prevalent medical condition principally among adolescents but can be present in any age group from newborns to the elderly. Scoliosis is a condition wherein the patient's spine curves from side to side, rotates, or collapses, and in some cases, more than one of these afflictions will be seen in a patient. In severe cases, when the spine curves, the rib cage, which is attached to the spine, will move along with the spine. This movement can cause various and possibly fatal lung issues, as the ribs can sometimes puncture a lung, or prod at the heart, reducing the functionality of these vital organs and putting the subject at risk. At around ages 10-14, children are typically tested by a pediatrician or a school nurse for scoliosis. However, it may be that some scoliosis has already been developing for months, even years before children undergo their first screening, and by then it may have developed into a curve too severe to treat without undergoing surgery. Also, the primary method of scoliosis curve monitoring is X-ray imaging. X-Ray imaging can be harmful and may cause cancer and various other health-related issues. X-ray imaging is not only dangerous but also costly, and some patients cannot afford to have repeated X-rays over short periods of time.

What is clearly needed is a low-cost apparatus and method to detect scoliosis without any chance of harm to the subject, and to detect frequently when curves have changed, since patients have to wait 6 months before finding out if their curve has improved or not. And also, to reduce long commutes for those who live far away from places that do specialized Scoliosis X-rays.

SUMMARY

One embodiment described herein is a computer-implemented method of detecting and quantifying a spinal curve. The method comprises obtaining a Forward-Looking Infrared Radiometer (FLIR) camera, calibrating the FLIR camera to room temperature, stabilizing the FLIR camera for imaging of a spine of a subject at a position horizontally spaced about ½ to about 3 meters, or about ½ to about 2 meters, from the camera, scanning at least a portion of the spine with the FLIR camera to obtain thermal data, and generating an image of the subject's spine using the thermal data.

In embodiments, the subject is scanned facing a blank, flat wall while situated between the FLIR camera and the wall. In some cases, the subject is scanned facing a blank wall corner while situated between the FLIR camera and the wall corner.

In some embodiments after images are generated, they are they are put through a machine learning software, which uses a classification algorithm to determine the subject's spinal curve.

Another embodiment described herein is a computer-implemented method of detecting and quantifying a spinal curve comprising obtaining an infrared radiometer camera, positioning the infrared radiometer camera for receiving thermal data for a spine of a subject, the camera being horizontally spaced about ½ meters to about 3 meters from the spine, scanning at least a portion of the spine with the infrared radiometer camera to obtain the thermal data, analyzing the thermal data using machine learning software which uses a classification algorithm to determine the presence of the spinal curve, and calculating a first Cobb angle for the curve of the subject's spine. In some cases, the machine learning software is configured to compare the Cobb angle to a prior Cobb angle for the subject's spine to detect whether the spinal curve has changed.

In embodiments, the spinal curve is further categorized as either a S or C type spinal curve. In some cases, the step of positioning comprises stabilizing the infrared radiometer camera on a stand. In embodiments, the method further comprises generating at least one image of the subject's spine using the thermal data.

In certain embodiment described herein, the machine learning program uses Convolutional Neural Networks for image recognition. These Convolutional Neural Networks may use feature extraction. In embodiments, the Convolutional Neural Networks are trained on multiple data sets, including a first data set comprising images of spines with no scoliotic curvature, a second data set comprising images of spines with moderate scoliotic curvature, and a third data set comprising images of spines with severe scoliotic curvature. In some cases, the digital images are taken with a smartphone that has a computer application containing the image-processing software.

DETAILED DESCRIPTION

The embodiments described herein provide a method, apparatus and system for efficiently and conveniently tracking changes in spinal curvature over time. The method provides for the collection of accurate data showing a degree of spinal curvature. In embodiments, the method incorporates machine learning technology to compare the degree of curvature to prior data for the same subject, or data of other subjects, or standardized data.

Figure 1A:
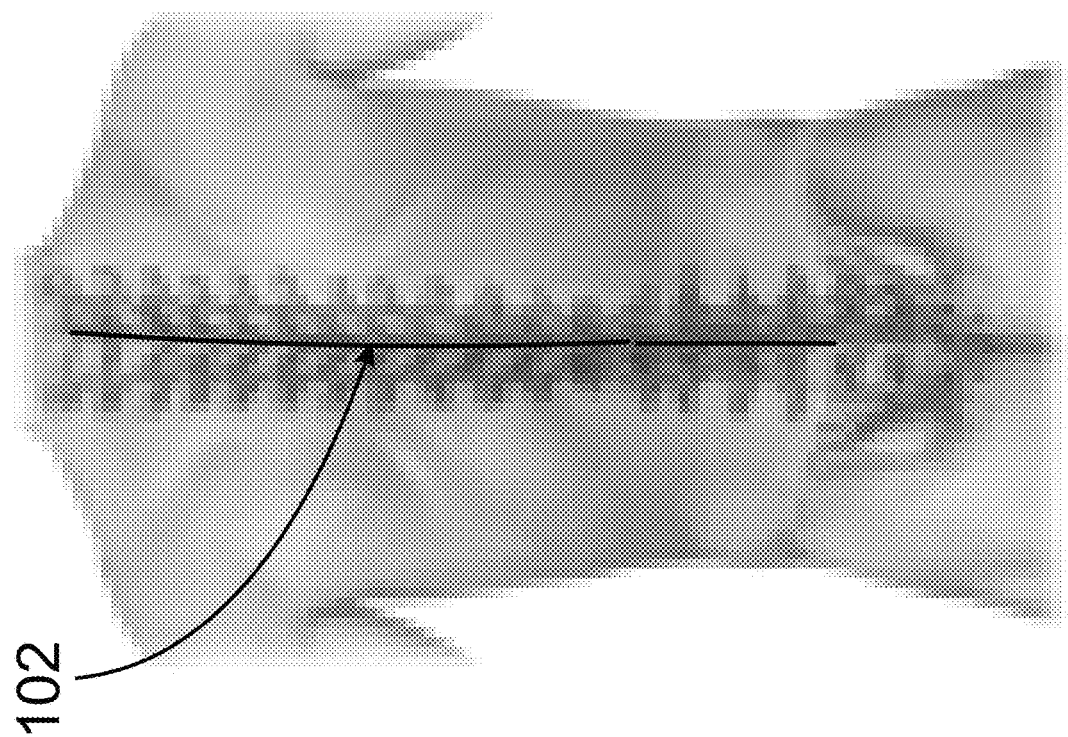
FIG. 1A is an upright view of a back of a person with pronounced Scoliosis.
Figure 1B:
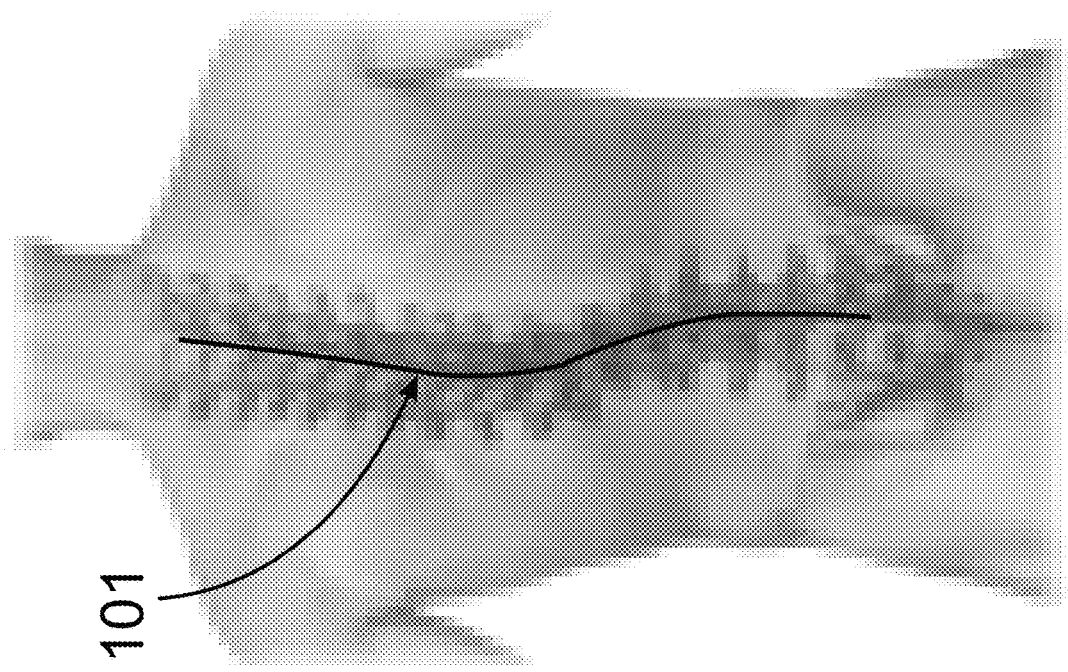
FIG. 1B is an upright image of a back of a person who does not have scoliosis.

FIG. 1A is an upright view of a back of a person with pronounced Scoliosis. The spinal curvature in this view has been traced with a solid line 101. FIG. 1B is an upright view of a back of a person without scoliosis, and the spinal curvature in FIG. 1B is also traced with a solid line 102. Comparing the solid-line traces illustrates the effect of scoliosis.

Figure 2:
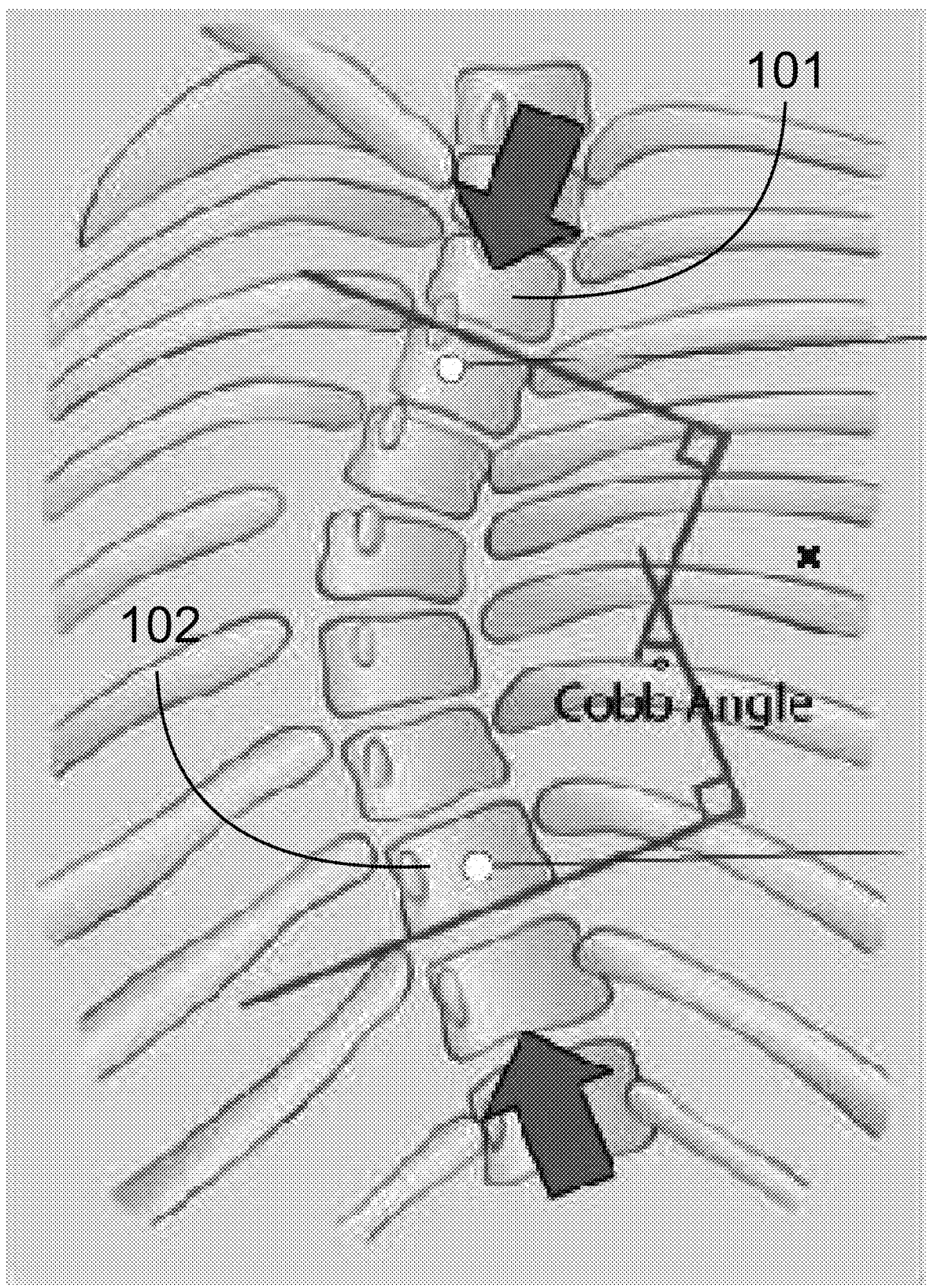
FIG. 2 is a diagram illustrating determination of Cobb Angle in scoliosis.

FIG. 2 is a diagram illustrating means of determining a Cobb angle as a measure of severity of scoliosis. In FIG. 2 a first straight line is drawn at a right angle to the spine at a vertebra that is the most displaced from the top of the spine, and a similar second line is drawn at a right angle to the spine at a vertebra that is the most displaced at the bottom of the spine. The angle between two other lines at right angled to the first and second lines, is the Cobb angle, and the greater the angle, the greater the degree of scoliosis. Many medical practitioners use the Cobb angle as representative to determine a point at which surgery is advisable. To measure Cobb angle in the conventional art one must do X-ray imaging. A Cobb angle of 10 degrees is regarded as a minimum angulation to define Scoliosis.

The inventor in this application has developed an apparatus and a method for determining presence of scoliosis and degree, without X-ray imaging. The inventor has developed apparatus and a method for imaging the human spine by irradiating a portion of a subject's back over the location of the spine, with infrared light.

Figure 3:
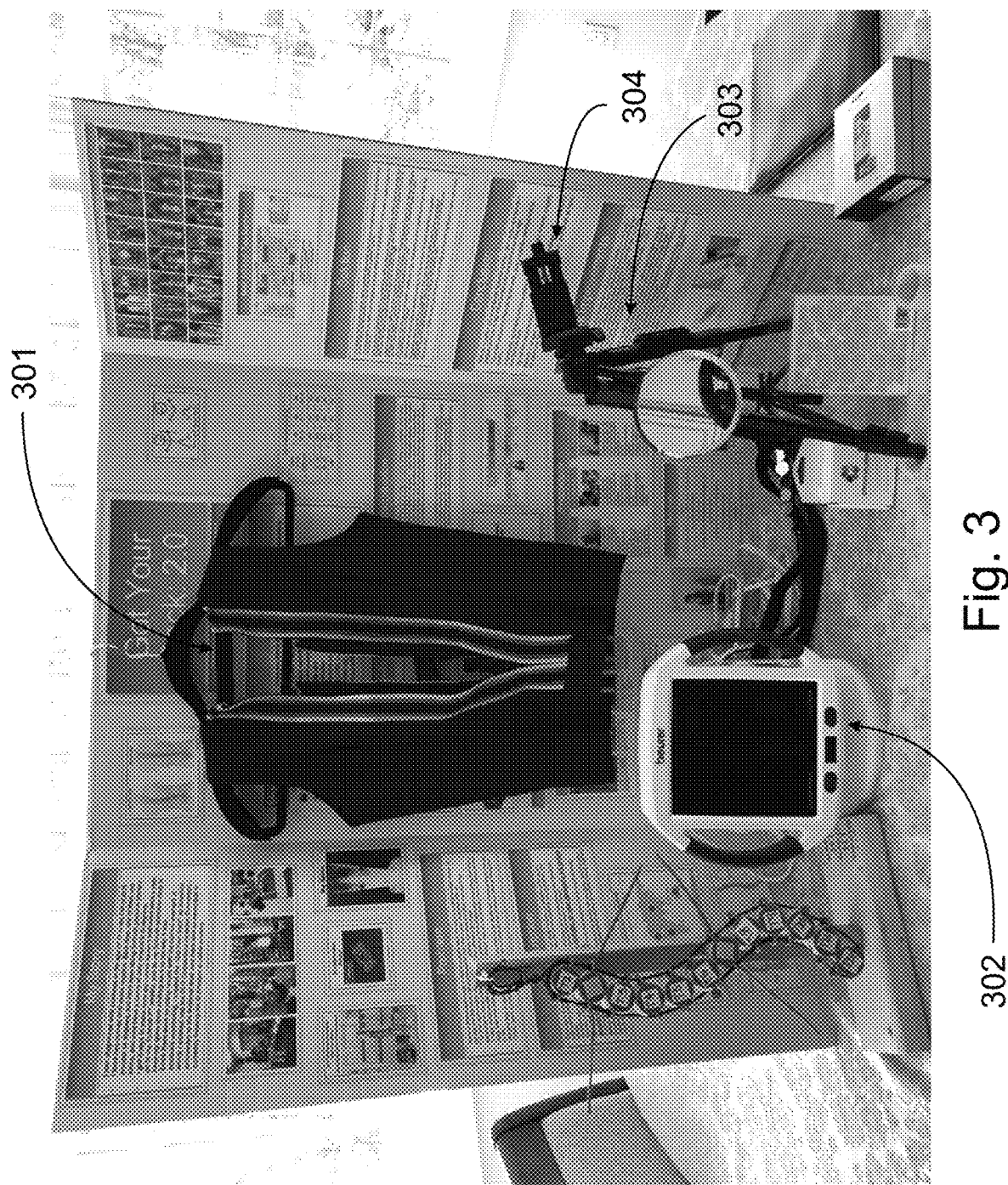
FIG. 3 is a display of apparatus used in practicing a first embodiment of the present invention.
Figure 4:
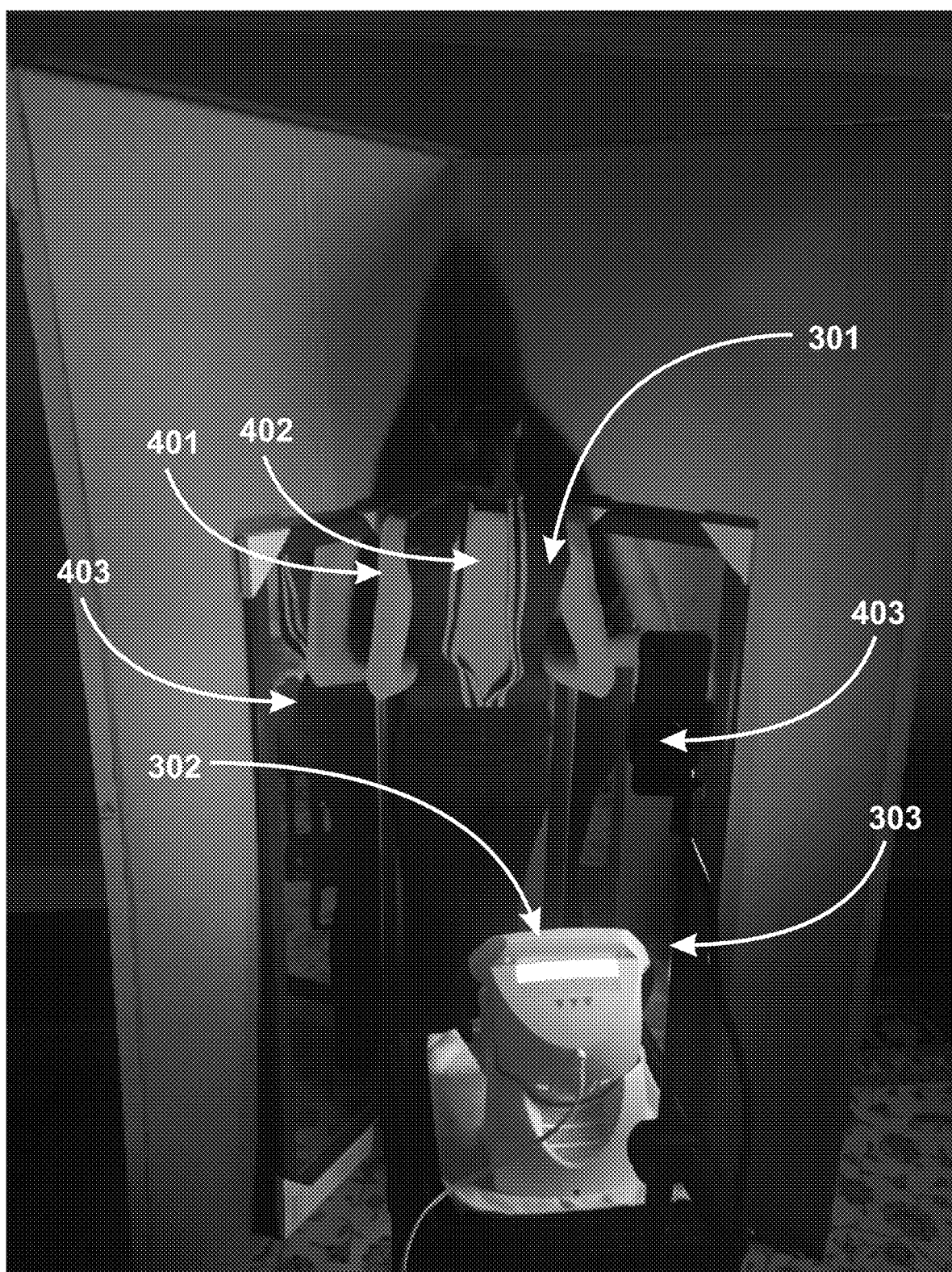
FIG. 4 is a view of a subject facing away from the figure viewpoint, relative to apparatus according to the first embodiment of the present invention.

FIG. 3 is a display of a first embodiment of an apparatus used in practicing the present invention. FIG. 4 is a view of a subject 401 facing away from the figure viewpoint, relative to apparatus according to an embodiment of the invention, the apparatus formed specifically of and comprising elements illustrated in FIG. 3.

In one embodiment of the invention a subject 401 (FIG. 4) for whom it is desired to image the spine to determine presence of scoliosis, and degree, dons a garment, in this example a vest 301, with purpose of focusing the camera on the spine. The vest has a vertical opening 402 as seen in the figure, which exposes that portion of the subject's back beneath which the spine is known to be.

The subject stands in a position between a pair of mirrors 403 (optional) facing into a corner, in this example, of a folded cardboard panel, facing away from an infrared heater 302 that is placed at a short distance behind the subject, with the heat emitting portion of the heater directed toward the subject, particularly that portion of the back exposed by the opening in the vest. The heater may be of several different sorts, but in this example is a Beurer™ 300-Watt infrared ceramic heater. In one example of the invention a Forward-Looking Infrared Radiometer (FLIR) camera 403 on a stand 303 is positioned behind and above the heater. In alternative embodiments a Near Infrared (NIR) camera may be used. There may also be other Infrared cameras that may be suitable. The height and position of the heater and the camera are both a matter of experimental result, but typically the heater and the camera need be within about 4 to 5 feet of the subject.

In some embodiments there may be an agent operating the camera manually. In other embodiments the camera may be set on a timer to activate. And in some embodiments the camera may be triggered wirelessly by a remote signal. The camera itself may be a special FLIR camera, or may be adapted from an iPhone, for example. When the pictures are taken, there may be a smartphone app that automatically processes the image and provides a Cobb angle calculation for patients to see how their curve has progressed. This app allows them to keep track of their curves as well as providing a graph of their progression over time.

Figure 5:
FIG. 5 is an image of a subject's spine taken in practice of the present invention.

FIG. 5 is an exemplary image taken using the exemplary setup illustrated in FIG. 4. The subject's spine is clearly visible, and the images are usable in determining presence and degree of scoliosis. And this is done without X-Ray, which is known to damage tissue, and to have a propensity, at large dosages, of causing cancer.

Figure 6:
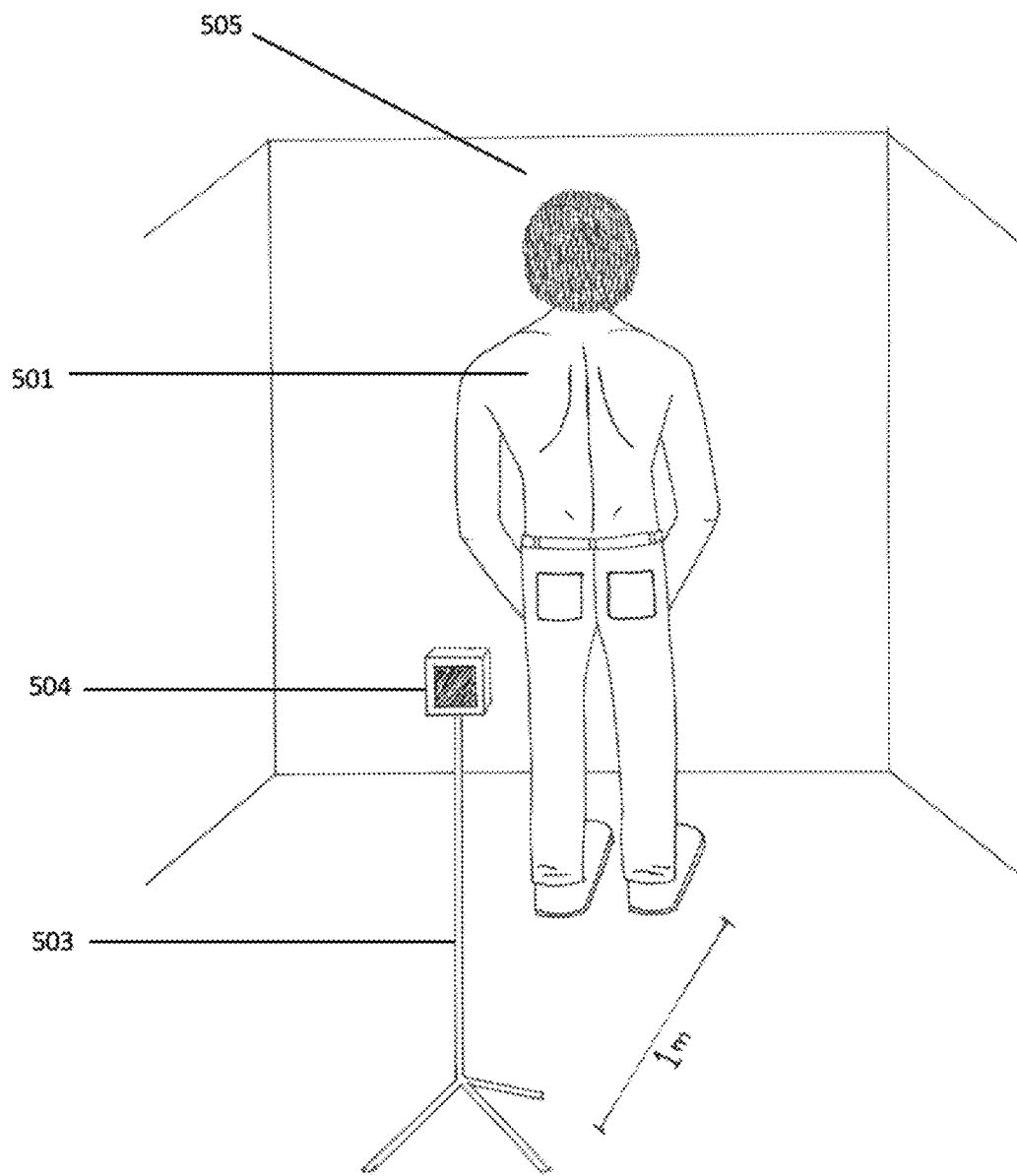
FIG. 6 is a display of apparatus used in practicing a second embodiment of the present invention with a subject facing away from the figure viewpoint.

FIG. 6 is a display of apparatus used in practicing a second embodiment of the present invention. It includes a view of a subject 501 facing away from the figure viewpoint, relative to apparatus according to a second embodiment of the invention, the apparatus formed specifically of and comprising elements illustrated in FIG. 6.

In this second embodiment, a subject 501, for whom it is desired to image the spine to determine presence and degree of scoliosis, stands in a position facing a flat, blank wall 505 at a short distance behind the camera 504. The front of the subject's feet is typically positioned at 0 to about 10 cm, or 0 to about 5 cm, away from the wall. The "blank" wall has a solid color, which is usually white, off-white or light gray. Other solid colors can be used as long as the color does not interfere with the clarity of the infrared image of the subject's spine. In one example of the invention, a Forward-Looking Infrared Radiometer (FLIR) camera is placed on a stand 503 and calibrated to room temperature (about 68-74° F. or about 70-72° F.), which typically will take about 20 minutes before photos are taken. The temperature of the room is kept at constant temperature. The subject stands about ½ to about 3 meters, or about ½ to about 2 meters, away from the camera, with the distance being measured from the back of the heel or shoe of the subject. The subject removes their shirt before scanning and has their back bare for about 10 minutes before images are to be taken.

In alternative embodiments a Near Infrared (NIR) camera may be used. Other infrared cameras may also be suitable. The height and position of the camera are a matter of experimental result, but typically the camera needs to be within one meter (about 4 to 5 feet) from the heels of the subject.

In embodiments, the FLIR camera has tools for changing color association relative to temperature. The FLIR camera includes a lens, and a housing containing a thermal sensor and processing electronics. In some cases, at least a portion of the processing electronics are contained in a separate device and the FLIR camera transmits data to the separate device. In embodiments, the camera is capable of detecting small differences in temperature of the subject's spine, e.g. differences of about 0.1° F., within the temperature range of about 65° F. to about 105° F. The field of view of the camera lens typically is at least 45 degrees. In embodiments, the FLIR camera has a resolution in the range of about 160×120 pixels with ±2% accuracy. In some cases, the FLIR camera has a thermal sensitivity or Noise Equivalent Temperature Difference (NETD) in the range of about 0.0 to about 0.11° F. In embodiments, the FLIR camera is longwave, with a spectral range of about 8 microns to about 14 microns. One non-limiting example of a FLIR camera that can be used is the FLIR E6 Infrared Camera with MSX®. In embodiments, the temperature of the subject's muscles surrounding the spine typically is in the range of about 90-93° F., or about 90.5-92.5° F. Higher temperature are detected when the subject has a greater degree of scoliosis as compared to a low degree of scoliosis or no scoliosis.

In some embodiments after images are generated, they are they are put through machine learning software, which uses a classification algorithm to determine the presence of the subject's spinal curve. The machine learning software can be used to determine whether the curve is an S curve or a C curve by comparing the new image to a training set stored in its database. After the initial comparison, it will then be compared to a narrower dataset of either S or C curve images. The program can be used to estimate the Cobb angle of the depicted curves. The data can be displayed as images, graphs, tables, pictures, etc.

In some embodiments that employ a vest, it may be 3-D printed from a suitable material which provides contrast and other image characteristics and in some cases will improve image results. In other embodiments, a vest is not used. In certain embodiments other software may be incorporated.

The skilled person will understand that the figures and descriptions of embodiments of the invention provided above are entirely exemplary, and that there will be many alterations that may be made in apparatus and in arrangement of elements within the scope of the invention. For example, the specific design of the vest is a preference rather than a strict requirement, and material of the vest may differ in different embodiments for different purposes. Also, there are several imaging devices that may be suitable, and several infrared heaters that may also be suitable, without significantly altering the results.

If a vest is used, the fabric for the vest may be, for example, cotton-polyester, which drapes well, and blocks infrared from parts of the body where heating is not wanted. If there are pockets behind the fabric, air in the pockets will heat, and may obscure images of the spine. There will be improvements made the vest to help reduce the scattering, as well as the way it sticks to the skin so there are fewer air pockets that appear due to the fabric not being tight enough or forming any curves. The vest could potentially be made of plastic, though the next model will likely be made of denim, which would block out Infrared a lot, and would have Velcro in the front to hold it together. The idea of adding tape to the back to make it stick better and reduce air pockets would be incorporated into this. The vest might also be 3-D printed from a suitable material.

The mirrors may not be used in some embodiments, and the angle of the mirrors may change. The purpose of the mirrors is to control scattering of infrared radiation.

One embodiment of the method is as follows:

Setup is made

Subject dons vest and assumed position

Camera is triggered multiple times, perhaps under different circumstances

Photos are uploaded to a computer executing image-processing software. The pictures can be taken directly in a smartphone app that will automatically do image processing and provide the Cobb angle. Uploading to a computer is not required in this case since the app will be doing all the work.

Photos are sorted for best quality

Best photos are used to determine presence and severity of Scoliosis

In another embodiment of the invention another step may be added, using a Python code with fifth-degree polynomials to graph the spinal curve, and from that curve use more code in order to determine the Cobb angle. This will be part of the function of the future smart phone app. Once the picture is taken, the app will figure out the curve by using fifth-degree polynomials.

In addition, in some advanced embodiments, is FEP (Fluorinated Ethylene Propylene) tape, which has an ability to disguise objects under an Infrared camera because of extraordinary temperature resistance, is used to outline the spine and the back, which enhances the clarity of the images. In addition, in some embodiments reflective stickers may be used. This might be part of the vest or standalone to reduce the scattering.

In some cases, the machine learning program uses Convolutional Neural Networks (CNNs) for image recognition. The CNN has a set of inputs, hidden layers, and a set of outputs. The hidden layers are used to detect different features in an image, such as edges, points, or patterns, and a final layer that connects the neurons from the last hidden layer to the output neurons. This CNN uses feature extraction, and is trained on several different data sets, including images of spines with no scoliotic curvature, moderate scoliotic curvature, and severe scoliotic curvature. For the data sets in the second and third categories, the images include (1) images of spines with S curves to the left, (2) images of spines with S curves to the right, (3) images of spines with C curves to the left, and (4) images of spines with C curves to the right. The CNN applies several filters to each image, including a first set of filters to determine whether or not there is curvature, and if so, a second set of filters to determine the precise shape and direction of that curvature. The shape and direction of the curvature are outputs. This analysis is followed by use of the third set of filters which recognize and/or determine the severity of the curvature. Finally, if the machine learning program determines that the spine is scoliotic, it calculates and outputs an approximation for the Cobb Angle by aggregating the data obtained by applying the first, second and third sets of filters and running the basic calculations for the Cobb Angle.

A number of alternatives, modifications, variations, or improvements therein may be subsequently made by those skilled in the art, which are also intended to be encompassed by the following claims.

What is claimed is:

1. A computer-implemented method of detecting and quantifying a spinal curve comprising:
   obtaining an infrared radiometer camera,
   positioning the infrared radiometer camera for receiving thermal data for a spine of a subject, the camera being horizontally spaced about ½ meters to about 3 meters from the spine,
   scanning at least a portion of the spine with the infrared radiometer camera to obtain the thermal data,
   analyzing the thermal data using machine learning software which uses a classification algorithm to determine the presence of the spinal curve, and
   calculating a first Cobb angle for the curve of the subject's spine.

2. The method of claim 1, wherein the machine learning software is configured to compare the Cobb angle to a prior Cobb angle for the subject's spine to detect whether the spinal curve has changed.

3. The method of claim 1, wherein the subject is scanned facing a blank wall while situated between the infrared radiometer camera and the blank wall.

4. The method of claim 1, wherein the subject is scanned facing a flat wall surface while situated between the infrared radiometer camera and the flat wall surface.

5. The method of claim 1, wherein the subject is scanned facing a wall corner while situated between the infrared radiometer camera and the wall corner.

6. The method of claim 1, wherein the spinal curve is further categorized as either a S or a C type spinal curve.

7. The method of claim 1, wherein the step of positioning comprises stabilizing the infrared radiometer camera on a stand.

8. The method of claim 1, further comprising generating at least one image of the subject's spine using the thermal data.

9. The method of claim 8, wherein the machine learning program uses Convolutional Neural Networks for image recognition.

10. The method of claim 9 wherein the Convolutional Neural Networks use feature extraction.

11. The method of claim 10, wherein the Convolutional Neural Networks are trained on multiple data sets, including a first data set comprising images of spines with no scoliotic curvature, a second data set comprising images of spines with moderate scoliotic curvature, and a third data set comprising images of spines with severe scoliotic curvature.

12. The method of claim 9, wherein digital images are uploaded to a computer configured to execute image-processing software.

13. The method of claim 9, wherein digital images are taken with a smartphone that has a computer application containing image-processing software.

\* \* \* \* \*